United States Patent [19]
Pynson et al.

[11] Patent Number: 5,879,319
[45] Date of Patent: Mar. 9, 1999

[54] SCLEROTOMY IMPLANT

[75] Inventors: Joël Pynson; Viviane Payrou, both of Toulouse; Bernard Feurer, Montlaur, all of France

[73] Assignee: Chauvin Opsia, Castanet Tolosan, France

[21] Appl. No.: 750,502

[22] PCT Filed: Jun. 20, 1995

[86] PCT No.: PCT/FR95/00818

§ 371 Date: Dec. 11, 1996

§ 102(e) Date: Dec. 11, 1996

[87] PCT Pub. No.: WO95/35078

PCT Pub. Date: Dec. 28, 1995

[30] Foreign Application Priority Data

Jun. 22, 1996 [FR] France .................................. 94. 07758

[51] Int. Cl.⁶ ...................................................... A61F 2/14
[52] U.S. Cl. ...................................................... 604/8; 623/4
[58] Field of Search .......................... 623/4, 5; 604/8–10, 604/294

[56] References Cited

U.S. PATENT DOCUMENTS

| | | | |
|---|---|---|---|
| 3,159,161 | 12/1964 | Ness | 604/8 |
| 4,521,210 | 6/1985 | Wong | 604/8 |
| 4,554,918 | 11/1985 | White | 604/10 |
| 4,787,885 | 11/1988 | Binder | 604/8 |
| 4,946,436 | 8/1990 | Smith | 604/8 |
| 5,073,163 | 12/1991 | Lippmann | 604/9 |
| 5,342,370 | 8/1994 | Simon et al. | 606/107 |
| 5,372,577 | 12/1994 | Ungerleider | 604/8 |
| 5,601,094 | 2/1997 | Reiss | 604/8 X |

FOREIGN PATENT DOCUMENTS

| | | |
|---|---|---|
| 2093736 | 1/1972 | France . |
| WO 91/07195 | 5/1991 | WIPO . |
| WO 92/00112 | 1/1992 | WIPO . |

OTHER PUBLICATIONS

Nancy Michel, "A wick that promotes fluid drainage treats glaucoma successfully in Russia", *Ocular Surgery News*, 1993, vol. 11, No. 23, p. 26.

M. Kamoun et al., "Microtrabeculoprothese", *Ophtalmologie* Vo. 2, 1988, pp. 227–229.

Hyun Bong Bae et al., "A Membranous Drainage Implant in Glaucoma Filtering Surgery: Animal Trial", *Korean J. Ophthalmol*, vol. 2, 1988, pp. 49–56.

*Primary Examiner*—David H. Willse
*Attorney, Agent, or Firm*—Young & Thompson

[57] ABSTRACT

A sclerotomy implant intended to be set in place in the sclera of the eye in order to provide for a continuous flow of aqueous humor through the trabecula for the treatment of a glaucoma. This implant is configured like a platelet made of biocompatible material and comprising an intrascleral portion (1) and a sub-conjuctival portion (5), the latter being adapted to come out of the sclera and penetrate under the conjunctiva. Retaining flanges (7a, 7b) provide for the blocking of the implant in the trap under the scleral flap. The implant comprises at least one continuous flow passage from its trabecular extremity (2) applied against the trabecula up to its external extremity (6) inserted in the conjunctiva.

8 Claims, 3 Drawing Sheets

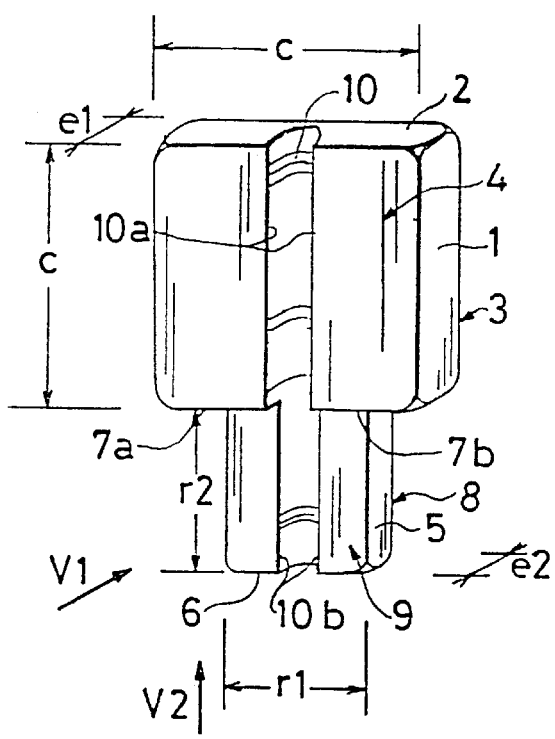
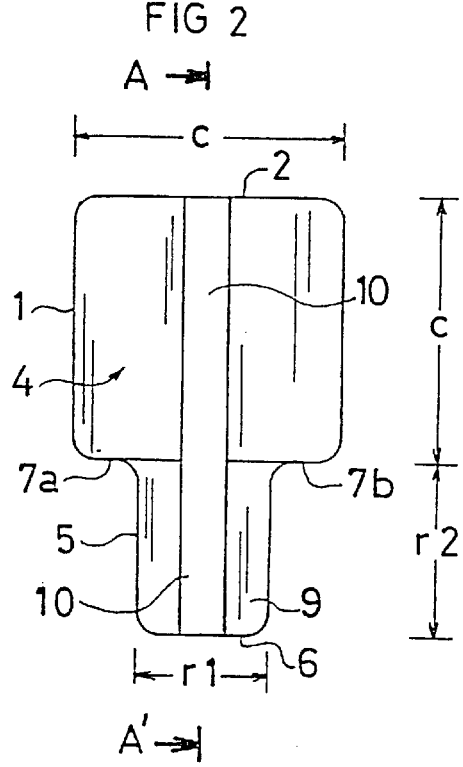
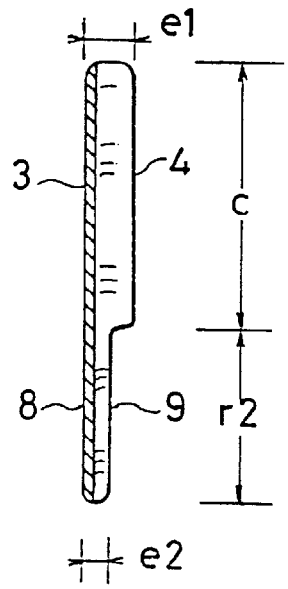
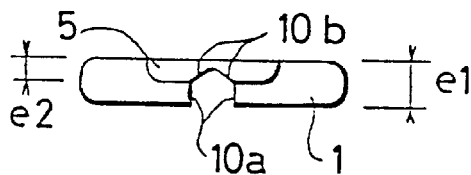

Fig 9
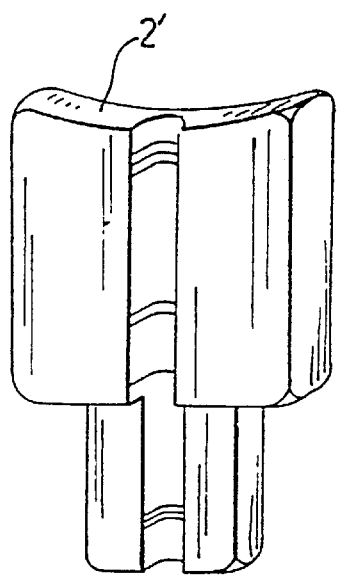
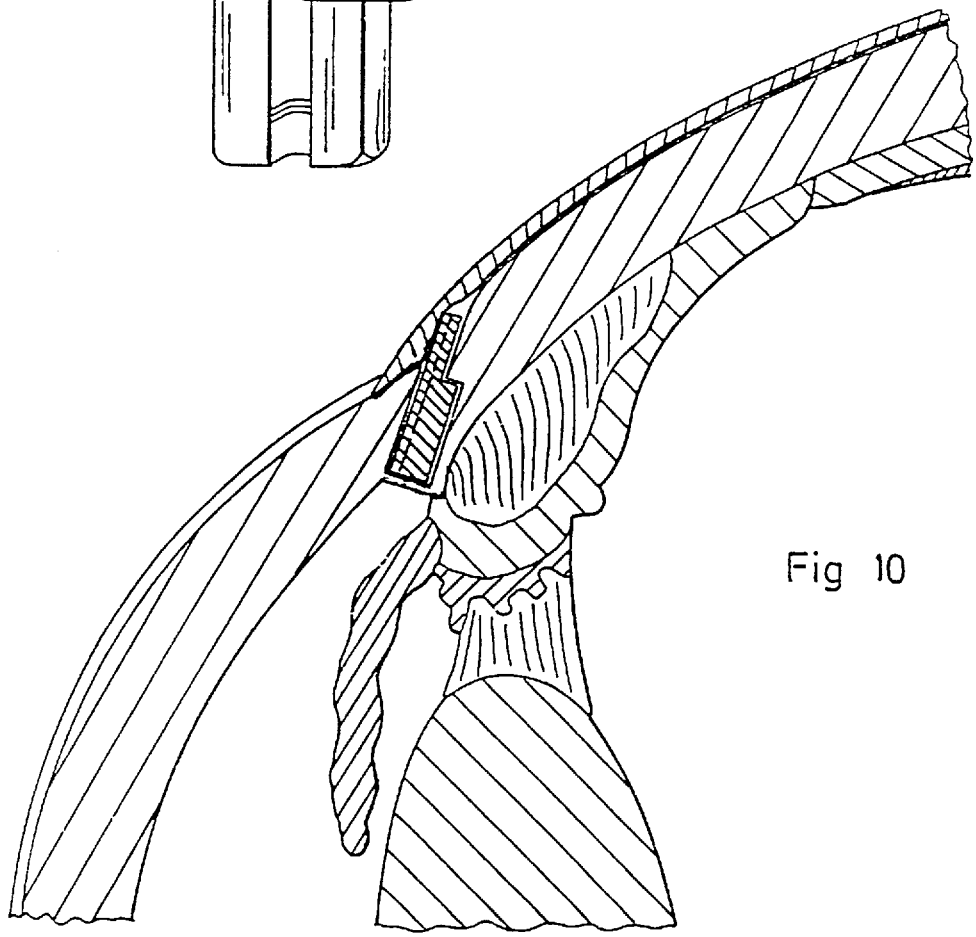
Fig 10

SCLEROTOMY IMPLANT

FIELD OF THE INVENTION

The invention concerns an implant intended to be inserted in the sclera of the eye following a sclerotomy operation with or without trabeculectomy.

BACKGROUND OF THE INVENTION

At the present time glaucoma is treated in the most serious cases by a surgical operation known as a trabeculectomy. This operation consists, following conjunctival disinsertion, of making an opening in the sclera by cutting out a scleral flap (division in the planes of the sclera as far as the trabeculum) and incising the trabeculum to enable the aqueous humor contained in the anterior chamber to flow out, thus reducing the intra-ocular pressure and limiting the pathological consequences of glaucoma. Such an operation, which has been performed for about fifteen years, generally produces a temporary improvement, but in time, healing of the scleral flap is liable to obstruct the flow of aqueous humor and a renewed increase in the intra-ocular pressure is then noted.

An attempt has been made to overcome this defect by applying antimitotic substances on the scleral flap so as to retard healing. However, the results are variable and it is even possible to observe an excessive flow of aqueous humor which can bring about too great a fall in the intra-ocular pressure.

Another type of operation is currently practiced for treating glaucoma. It consists of putting a valve in place associated with a tube which emerges in the anterior chamber to enable aqueous humor to flow out in the case of an increase in pressure in this chamber. This technique has disadvantages however. In the first place, it requires a complex operation affecting the anterior chamber, with the risk of a deleterious effect on the corneal endothelium, and surgeons who are used to trabeculotemies are reluctant to perform this type of complex and risky surgical operation. Moreover, the tube tends to block up so that the efficiency of the device, which is good after it has been put in place, decreases rapidly with time. In addition, the pipe is sometimes expelled from the anterior chamber. It should be noted that these valves have a relatively complex structure which makes them costly to manufacture.

In addition, several publications have proposed novel techniques which are at the experimental stage (or have remained at the experimental stage on account of basic defects) and which consist of inserting an implant under the scleral flap with a view to preventing the flow of aqueous humor through the incision in the trabeculum from being obstructed too rapidly.

A first technique is described in the following publication "Hyun Bong Bae et al., A Membranous Drainage Implant in Glaucoma Filtering Surgery: Animal Trial, Kor. J. Ophthalmol., vol. 2, 1988, 49–56". It consists of placing a hydrophobic membrane under the scleral flap which penetrates into the anterior chamber by means of an incision in the trabeculum. By virtue of its hydrophobic nature, this membrane opposes the formation of fibroses close to its surface and enables aqueous humor to flow out along it. However the permanent flow thus produced is small and the presence of such a membrane appears to be insufficient to restore the intra-ocular pressure to a normal value. Moreover, its insertion involves an operation on the anterior chamber with risks to the corneal endothelium, this operation being much more delicate than a simple trabeculectomy as already indicated.

The following publication: "M. Kamoun et al., Microtrabéculoprothèse, Ophtalmologie, 1988, vol. 2, 227–229", describes a trabeculoprosthesis made of a very hydrophilic porous hydrogel which is put in place in the dry state in the sclera so as to penetrate the incision in the trabeculum by a tapered part. Hydration causes the hydrogel to swell and the incision to be hermetically sealed. The aqueous humor then flows out through pores in the material from the anterior chamber to the sclera. This filtration though a porous material of this type brings about a reduction in the intra-ocular pressure. However, the aforementioned defect, which lies in a rapid obstruction of the flow, is not overcome by this prosthesis, since fibroses which form in the sclera rapidly lead to obstruction of the flow. Moreover, as in the previous technique, insertion of this prosthesis affects the endothelium because a tapered part of the prosthesis is made to penetrate inside the anterior chamber.

U.S. Pat. No. 4,521,210 describes an implant with an elongated shape which is placed above the choroid at the interface between this and the sclera. This implant has a tapered part which penetrates the anterior chamber. It has the same disadvantages as the previous one, even though its long length and the hole and passages provided in it ensure better discharge of the aqueous humor. In addition, its insertion would appear to be extremely delicate, considering the dimensions of this implant and its position at the choroid/sclera interface.

Another implant is described in the following publication "Nancy Michel, A Wick that promotes fluid drainage treats glaucoma successfully in Russia, Ocular Surgery News 1993, vol. 11 (23) p 26". This implant consists of a bundle of reabsorbable fibres which is put in place under the scleral flap facing the incision in the trabeculum. The inventors have very little information on this technique which has been proposed very recently. However, it is probable that such an implant of a biological origin (pig), buried in the sclera, will experience the same blockage problems as the previous implants. Moreover, displacements in the opening, or even expulsion, are to be feared.

Another implant is described in International Application PCT/US 90/06216. This implant, inserted in the sclera, does not resolve the aforementioned defect of blockage of the flow by the fibroses which form in this tissue.

It should be noted that all the known implants previously referred to are put in place following a trabeculectomy during which the trabeculum is incised.

OBJECTS OF THE INVENTION

The present invention proposes to provide a novel implant overcoming the aforementioned defects and having a long-lasting effect in glaucoma therapy.

A first objective of the invention is to provide an implant which enables a satisfactory flow of the aqueous humor from the anterior chamber to occur, a continuous flow which is less subject to risks of obstruction with time.

Another objective is to provide an implant which can be put in place, either by a simple sclerotomy operation during which the trabeculum is untouched, or by a trabeculectomy operation which does not affect the anterior chamber of the eye and the corneal endothelium (this operation, which does not necessarily involve a trabeculectomy, will be referred to as a "sclerotomy implant").

Another objective is to provide an implant which is not subject to the risks of displacement or expulsion.

Another objective is to provide an implant with a simple structure which lends itself to easy manufacture.

SUMMARY OF THE INVENTION

For this purpose, the sclerotomy implant aimed at in the present invention is in the form of a tab made of a biocompatible material, wherein it comprises:

a first end, a so-called trabecular end, adapted to be positioned against the trabeculum, which may be left intact or be subjected to a trabeculectomy as in traditional techniques, a first part, a so-called intra-scleral part, carrying the trabecular end and adapted so that it can be inserted into the opening under the scleral flap, a second part, a so-called sub-conjunctival part, extending the intra-scleral part and adapted to leave the sclera and to be positioned under the conjunctiva in contact with this, stops situated at the junction between the intra-scleral part and the sub-conjunctival part and adapted so that the said intra-scleral part can be locked in the opening, a second end, a so-called external end, opposite the trabecular end and carried by the sub-conjunctival part, means of continuous flow extending along the intra-scleral part and the sub-conjunctival part between the trabecular end and the external end with a view to enabling the aqueous humor to flow from the trabeculum to the conjunctiva, either by filtration through the trabeculum if this is left intact, or by an incision made in the case of a trabeculectomy.

According to a first embodiment, these means of continuous flow comprise at least one continuous groove made along the intra-scleral part and the sub-conjunctival part so as to emerge at the trabecular end and the external end.

The implant may also be made of a porous material, the means of continuous flow consisting of internal passages derived from the porosity of the material.

According to a preferred embodiment, the two types of means of flow are combined: the material of the implant is porous and the means of flow comprises, firstly, at least one continuous groove made along the intra-scleral part and the sub-conjunctival part, and secondly, internal passages derived from the porosity of the material.

According to another advantageous feature of the invention, the trabecular end has a concave shape with a radius of curvature substantially between 4 mm and 8 mm. This end thus matches the shape of the trabeculum with which it is placed in contact, which encourages the collection of the aqueous humor and its discharge through the means of flow of the implant (in particular in the absence of trabeculectomy, in the case where the trabeculum is left intact).

The stops situated at the junction between the intra-scleral part and the sub-conjunctival part preferably comprise shoulders, situated either side of the intra-scleral part and defined by having the width of the said intra-scleral part greater than that of the sub-conjunctival part. As will be seen below, these shoulders cooperate with the sutures which are made at the end of the operation to hold the scleral flap in the opening above the implant. The intra-scleral part thus is locked in a stable position between the trabeculum and these sutures. In this position, the sub-conjunctival part which extends the said intra-scleral part, is positioned under the conjunctiva in contact with this and enables the aqueous humor circulating in the means of flow of the implant to leave the sclera to flow under the conjunctiva without risk of blockage.

BRIEF DESCRIPTION OF THE DRAWINGS

Other features and advantages of the invention will become apparent from the following description with reference to the accompanying drawings, which show, in a non limiting manner, two embodiments of implants according to the invention and which illustrate the use of these for the treatment of glaucoma of the eye. In these drawings:

FIGS. 1, 2, 3 and 4 show, respectively, at a very enlarged scale of about 10: an implant in perspective, a front view along $V_1$, a section AA' and a view from below along $V_2$, FIG. 9 shows a variant of the implant in perspective, FIG. 10 illustrates this implant inserted at the end of a simple sclerotomy operation not affecting the trabeculum.

DETAILED DESCRIPTION OF THE INVENTION

Figure 5:
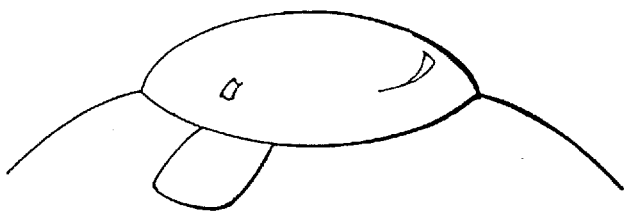
FIGS. 5, 6, 7 and 8 show diagrammatically the insertion of the said implant during a trabeculectomy.

The implant shown by way of example in FIGS. 1 to 4 is in the form of a thin elongated tab made of a biocompatible material, in particular a methylmethacrylate/vinylpyrrolidone copolymer. The relative proportions of these two compounds are in particular about 48% and 52%. Such a copolymer has a high porosity which may be measured by its hydrophilic ratio which is of the order of 40% (mass of water able to be absorbed relative to the mass of dry copolymer). The dimensions provided below, in a non limiting manner, correspond to the hydrated implant and are reduced by about 20% when the implant is dry.

The implant comprises substantially two parts with the general shape of a rectangular parallelepiped: an intra-scleral part 1 and a sub-conjunctival part 5 which is narrower than the first.

The intra-scleral part is provided with a trabecular end 2, in the example having a flat shape, which is intended to be positioned facing the trabeculum and the dimensions of which are greater than those of the incision (which in this example will be made in the trabeculum) so as to be stopped by the trabeculum. This end has in practice a width -c- substantially between 2 mm and 4 mm, in the example equal to 3 mm (to approximately ±20%) so as to overlap either side of the incision in the trabeculum (the length of which is always less than 2 mm).

The intra-scleral part 1 possesses a so-called upper face 3 and a so-called lower face 4 having a substantially square shape with a side -c- equal to 3 mm (to approximately ±20%). The thickness $e_1$ of the said intra-scleral part is in particular 0.50 mm (to approximately ±20%).

The sub-conjunctival part 5 which extends the intra-scleral part described above terminates in a so-called external end 6 and has dimensions less than those of the intra-scleral part. The junction between the two parts defines two shoulders 7a, 7b situated either side of the intra-scleral part. These shoulders are intended to operate as stops ensuring that the implant is locked in place when stitching is carried out at the end of the operation.

The sub-conjunctival part 5 possesses an upper face 8 and a lower face 9 with a rectangular shape, having a side $r_1$ equal to 1.5 mm (to approximately ±20%) in the width direction and a side $r_2$ equal to 2 mm (to approximately ±20%) in the length direction.

The sub-conjunctival part possesses a thickness -$e_2$- which is in particular equal to 0.25 mm (to approximately ±20%) (of the order of half the thickness -$e_1$- of the intra-scleral part).

As the figures show, the intra-scleral and sub-conjunctival parts possess, in the example shown, upper faces 3 and 8 situated substantially in the same plane, and opposite lower faces 4 and 9 which are offset so that the lower face of the sub-conjunctival part 5 is recessed in relation to that of the intra-scleral part 1.

In addition, a continuous groove 10 is provided along the implant in the intra-scleral part 1 and the sub-conjunctival part 5 so as to emerge, either side of the implant, at the trabecular end 2 and the external end 6. This groove is arranged in the example along the axis of the implant and possesses a section, the bottom of which has a circular shaped section or is an open angle. In the intra-scleral part 1, it opens onto the lower face 4 through a portion 10a with parallel faces, whereas it opens onto the lower face 9 of the sub-conjunctival part through divergent faces 10b.

The tab described above is used as a sclerotomy implant (with or without trabeculectomy) for treating glaucoma of the eye by means of an implant in the eye such that:

the trabecular end 2 is positioned against the trabeculum and stopped by the latter without penetrating the anterior chamber, the sub-conjunctival part 5 is placed under the conjunctiva in contact with this, the stops 7a, 7b cooperate with the sutures $S_1$, $S_2$ to ensure that the sub-conjunctival part 1 is locked in the opening T.

FIGS. 5 to 8 illustrate insertion into the eye in the case where a trabeculectomy is carried out. The implant is previously impregnated with an aqueous solution until saturated.

Figure 6:
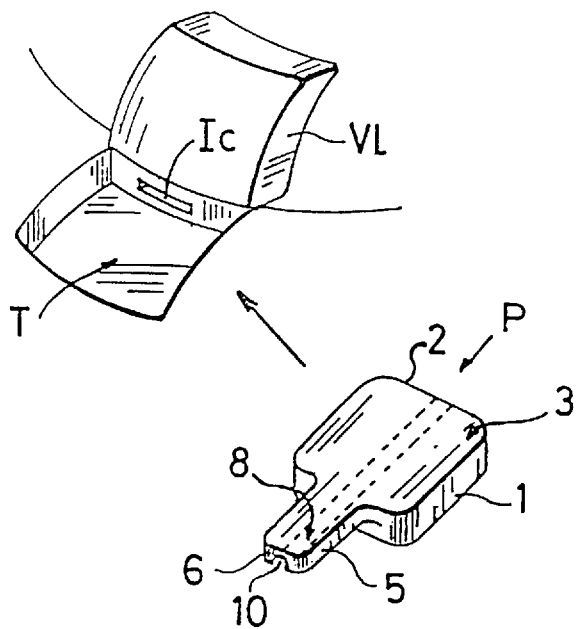

By means of a sclerotomy operation, after conjunctival disinsertion, a scleral flap $V_1$ is cut out from the sclera so as to produce an opening T. The trabeculum is then incised. FIG. 6 shows this incision in $I_c$.

The implant P is presented as shown in this figure with its trabecular end 2 beside the trabeculum and its external end 6 beside the conjunctiva. The upper face 3, 8 is positioned above the tissues and the lower face 4, 9, which is provided with the groove 10, is situated facing the tissues.

Figure 7:
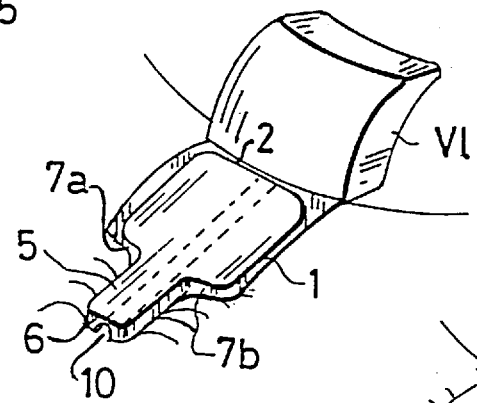
Figure 8:
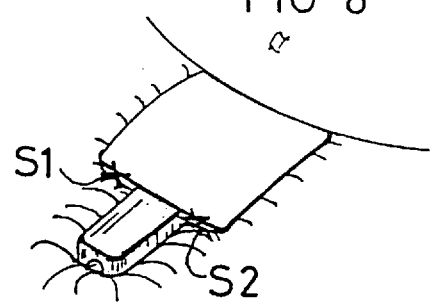

As shown in FIG. 7, the implant is inserted in the eye so that the intra-scleral part 1 is embedded in the opening T with its trabecular end 2 against the trabeculum facing the incision $I_c$, and so that its sub-conjunctival part 5 rests against the conjunctiva outside the opening. In this position, the external end 6 is situated outside the sclera against the conjunctiva.

The scleral flap $V_1$ is then folded down towards the opening and the sutures $S_1$, $S_2$ are made in the hollows of the shoulders 7a and 7b of the implant so as to attach the flap to the sclera. The intra-scleral part of the implant is then locked in the opening between the trabeculum and these sutures. The conjunctiva may then be made to cover the assembly in a conventional manner.

The groove 10 and the pores of the copolymer produce a continuous flow path between the trabecular incision and the conjunctiva without risk of blockage whatever the formation of fibroses in the sclera.

It should be emphasized that the surgical operation summarized above is of a traditional type and it does not affect the anterior chamber nor does it present any risk to the corneal endothelium.

FIG. 9 shows a variant of the implant, the characteristics of which are identical to the preceding one, with the exception of the shape of the trabecular end, indicated by reference 2' in this figure. This end is concave, substantially cylindrical, with a radius of curvature substantially equal to 6 mm (to approximately ±20%).

The insertion operation is similar to the preceding one with the exception that the incision in the trabeculum is not made. The trabecular end is arranged to be in contact with the trabeculum so as to match the shape of the surface of the latter. The passage of humor from the anterior chamber occurs by filtration through the trabeculum.

FIG. 10 illustrates a section of the implant in position. It is essential to note that its sub-conjunctival part leaves the sclera and is lodged under the conjunctiva. Thus, the external end causes the aqueous humor to flow under the conjunctiva, and forms a filtration bulla under the latter. This bulla serves to indicate the efficiency of the implant. Visible through the conjunctiva, it makes it possible to verify that the flow is occurring correctly.

We claim:

1. A sclerotomy implant intended to enable aqueous humor to flow continuously through a trabeculum, said implant being in the form of a tab made of a biocompatible material, and comprising:

a trabecular end adapted to be positioned against the trabeculum;

an intra-scleral part, carrying the trabecular end and adapted to be inserted into an opening under a scleral flap;

sub-conjunctival part, extending the intra-scleral part and having a thickness less than that of the intra-scleral part, said sub-conjunctival part adapted to leave the sclera and be positioned under the conjunctiva in contact therewith;

the intra-scleral part and the sub-conjunctival part having lower faces offset so that the lower face of the sub-conjunctival part is recessed in relation to the lower face of the intra-scleral part;

stops situated at the junction between the intra-scleral part and the sub-conjunctival part, and adapted to lock said intra-scleral part in the opening;

an external end, opposite the trabecular end, and carried by the sub-conjunctival part;

flow means, comprising at least one continuous groove extending along the intra-scleral part and the sub-conjunctival part between the trabecular end and the external end, for enabling flow of the aqueous humor from the trabeculum to the conjunctiva; and wherein the intra-scleral part and the sub-conjunctival part possess upper faces situated substantially in the same plane, and the lower faces are provided with said at least one groove.

2. The implant according to claim 1, wherein the implant is made of a porous material, and the flow means comprise internal passages derived from the porosity of the material.

3. The implant according to claim 1, wherein the thickness ±20% of the sub-conjunctival part is equal to half the thickness ±20% of the intra-scleral part.

4. The implant according to claim 1, wherein the trabecular end has a concave shape with a radius of curvature substantially between 4 mm and 8 mm.

5. The implant according to claim 1, wherein the width of the trabecular end is substantially between 2 mm and 4 mm.

6. The implant according to claim 1, wherein the stops comprise shoulders situated on either side of the intra-scleral part, and having the width of the intra-scleral part.

7. The implant according to claim 6, wherein the intra-scleral part has a substantially square front section with a side equal to 3 mm±20%, and the sub-conjunctival part has a substantially rectangular section having a width equal to 1.5 mm±20%, and a length equal to 2 mm±20%.

8. The implant according to claim 1, wherein the implant is made of a methylmethacrylate vinylpyrrolidone copolymer.

* * * * *

UNITED STATES PATENT AND TRADEMARK OFFICE
CERTIFICATE OF CORRECTION

PATENT NO. : 5,879,319
DATED : March 9, 1999
INVENTOR(S) : Joël PYNSON et al.

It is certified that error appears in the above-indentified patent and that said Letters Patent is hereby corrected as shown below:

On the title page, in Item [30], change the date "Jun. 22, 1996" to --Jun. 22, 1994--.

Signed and Sealed this

Seventh Day of September, 1999

Attest:

Q. TODD DICKINSON

Attesting Officer     Acting Commissioner of Patents and Trademarks